(12) United States Patent
Tracy

(10) Patent No.: US 6,881,207 B1
(45) Date of Patent: Apr. 19, 2005

(54) DISPOSABLE DIAPER WITH PADDED WAISTBAND AND LEGHOLES

(76) Inventor: Rhonda Tracy, 233 Grandview, Glen Ellyn, IL (US) 60137

( * ) Notice: Subject to any disclaimer, the term of this patent is extended or adjusted under 35 U.S.C. 154(b) by 0 days.

(21) Appl. No.: 09/107,643

(22) Filed: Jun. 30, 1998

Related U.S. Application Data

(63) Continuation of application No. 08/092,540, filed on Jul. 16, 1993, now Pat. No. 5,797,824, which is a continuation of application No. 07/790,469, filed on Nov. 12, 1991, now abandoned, which is a continuation of application No. 07/516,473, filed on Apr. 30, 1990, now Pat. No. 5,064,421, which is a continuation-in-part of application No. 07/093,681, filed on Sep. 8, 1987, now abandoned.

(51) Int. Cl.$^7$ ................................................ A61F 13/15
(52) U.S. Cl. ......................... 604/385.3; 604/385.25; 604/385.24; 604/385.29
(58) Field of Search .................. 604/358, 367, 604/369, 370, 373, 374, 385.01, 385.03, 385.21, 385.23, 385.24, 385.25, 385.29, 385.3, 385.31, 385.1, 385.2

(56) References Cited

U.S. PATENT DOCUMENTS

| | | | |
|---|---|---|---|
| 1,329,119 A | | 1/1920 | George |
| 2,649,858 A | | 8/1953 | Le Bolt |
| 3,237,625 A | | 3/1966 | Johnson |
| 3,417,751 A | | 12/1968 | Murdoch |
| 3,461,872 A | | 8/1969 | McConnell |
| 3,489,148 A | * | 1/1970 | Duncan et al. ............ 604/382 |
| 3,568,676 A | | 3/1971 | Del Guerco |
| 3,572,342 A | * | 3/1971 | Lindquist .................... 604/373 |
| 3,612,055 A | | 10/1971 | Mesek et al. |
| 3,658,064 A | | 4/1972 | Pociluyko |
| 3,842,837 A | | 10/1974 | Sward |
| 3,882,870 A | | 5/1975 | Hathaway |
| 3,896,807 A | * | 7/1975 | Buchelter ................... 604/289 |
| 3,951,150 A | | 4/1976 | Schaar |
| 3,987,794 A | | 10/1976 | Schaar |
| 3,990,450 A | | 11/1976 | Schaar |
| 3,995,637 A | | 12/1976 | Schaar |
| 3,995,638 A | | 12/1976 | Schaar |
| 3,995,640 A | | 12/1976 | Schaar |
| 4,014,338 A | | 3/1977 | Schaar |
| 4,041,949 A | | 8/1977 | Kozak |
| 4,102,340 A | | 7/1978 | Mesek et al. |
| 4,230,113 A | | 10/1980 | Mehtas |
| 4,246,900 A | | 1/1981 | Schroder |
| 4,324,245 A | | 4/1982 | Mesek et al. |
| 4,326,528 A | | 4/1982 | Ryan et al. |
| 4,341,216 A | | 7/1982 | Obenour |
| 4,352,355 A | | 10/1982 | Mesek et al. |

(Continued)

FOREIGN PATENT DOCUMENTS

| | | | |
|---|---|---|---|
| EP | 02159693 A | 12/1985 | ........... A41B/13/02 |
| EP | 0219969 A1 | 10/1986 | |
| GB | 2136677 | 3/1984 | |
| GB | 2159693 A | 6/1985 | |
| GB | 2136678 B | 7/1986 | |
| GB | 2136677 B | 12/1986 | |
| GB | 2188532 B | 1/1990 | |
| GB | 2189133 B | 11/1990 | |

OTHER PUBLICATIONS

Webster's Dictionary (1979).*
Absorbent Products Conference, insight 86, International Conferences, Sep. 10–11, 1986, sponsored by Marketing/Technology Service, Inc.

(Continued)

*Primary Examiner*—Jacqueline F. Stephens
(74) *Attorney, Agent, or Firm*—Barnes & Thornburg LLP

(57) ABSTRACT

A disposable diaper having a front section, rear section, crotch portion, and a waist band. A soft padding is provided on the waist band. Padding is also provided on the edge portions surrounding the leg holes.

2 Claims, 1 Drawing Sheet

U.S. PATENT DOCUMENTS

| | | |
|---|---|---|
| 4,388,075 A | 6/1983 | Mesek et al. |
| 4,425,127 A | 1/1984 | Suzuki et al. |
| 4,490,148 A | 12/1984 | Beckestrom |
| 4,515,595 A | 5/1985 | Kievit et al. |
| RE31,922 E | 6/1985 | Mesek et al. |
| 4,527,989 A | 7/1985 | Karami |
| 4,552,795 A | 11/1985 | Hansen et al. |
| 4,568,344 A | 2/1986 | Suzuki et al. |
| 4,642,819 A | 2/1987 | Ales et al. |
| 4,657,539 A | 4/1987 | Hasse |
| 4,670,011 A | 6/1987 | Mesek |
| 4,681,580 A | 7/1987 | Reising et al. |
| 4,695,278 A | 9/1987 | Lawson |
| 4,699,621 A | 10/1987 | Stevens et al. |
| 4,701,170 A | 10/1987 | Wilson et al. |
| 4,701,172 A | 10/1987 | Stevens |
| 4,701,173 A | 10/1987 | Zehner et al. |
| 4,710,187 A | 12/1987 | Boland et al. |
| 4,718,900 A | 1/1988 | Boland et al. |
| 4,728,326 A | 3/1988 | Gilles |
| 4,738,677 A | 4/1988 | Foreman |
| 4,743,239 A | 5/1988 | Cole |
| 4,743,241 A | 5/1988 | Igaue et al. |
| 4,743,246 A | 5/1988 | Lawson |
| 4,753,643 A | 6/1988 | Kassai |
| 4,753,645 A | 6/1988 | Johnson |
| 4,753,646 A | 6/1988 | Enloe |
| 4,770,656 A | 9/1988 | Proxmire et al. |
| 4,816,025 A * | 3/1989 | Foreman ............... 604/385.2 |
| 4,838,885 A | 6/1989 | Bernardin |
| 4,861,652 A | 8/1989 | Lippert et al. |
| 4,978,570 A | 12/1990 | Heys et al. |
| 5,026,364 A | 6/1991 | Robertson |
| 5,064,421 A | 11/1991 | Tracy |
| 5,207,662 A | 5/1993 | James |
| 5,324,277 A | 6/1994 | Daugan et al. |
| 5,435,806 A | 7/1995 | Daugan et al. |
| 5,797,824 A * | 8/1998 | Tracy ..................... 604/385.1 |

OTHER PUBLICATIONS

Absorbent Products Conference, insight 82, International Conferences, Oct. 13–14, 1982, sponsored by Marketing/Technology Service, Inc.

Absorbent Products Conference, insight 87, International Conferences, Sep. 23–24, 1987, sponsored by Marketing/Technology Service, Inc.

Absorbent Products Markets, Update 84, Part 1, (Tampons, Diapers, Feminine Pads), vol. 1 Diapers, Published by Marketing/Technology Service, Dec. 1984.

New Movement of Disposable Diapers in Japan, Akira Takeuchi, Uni–Charm Corporation, Section II, Section II–9.

* cited by examiner

DISPOSABLE DIAPER WITH PADDED WAISTBAND AND LEGHOLES

This application is a continuation of application Ser. No. 08/092,540 filed on Jul. 16, 1993, now U.S. Pat. No. 5,797,824 which is a continuation of Ser. No. 07/790,469 filed on Nov. 12, 1991, now abandoned which is a continuation of Ser. No. 07/516,473 filed Apr. 30, 1990 (now U.S. Pat. No. 5,064,421), which is a continuation-in-part of Ser. No. 07/093,681 filed Sep. 8, 1987, now abandoned.

BACKGROUND OF THE INVENTION

1. Field of the Invention

This invention relates in general to a disposable diaper and more specifically, to a disposable diaper having a padded waistband and legholes.

2. Description of the Prior Art

Disposable diapers have largely replaced the common cloth diaper to be worn by infants and toddlers. Disposable diapers not only can be easily discarded, but are adjustable and convenient to attach and remove. Known diapers of the disposable variety are typically capable of effective retention of liquid and solid material without having to resort to protective covers as was required by cloth diapers. Although known disposable diaper designs are generally satisfactory, several problems haven arisen in their use. The waist band and border around the legholes of prior art disposable diapers are commonly an unprotected plastic band and the like. Such bands are uncomfortable when worn and often such material is stiff, and scratches and abrades an infant's skin. In addition, known waist bands and leg bands in disposable diapers do not provide an optimum barrier against leakage and seepage, which is so desirable.

SUMMARY OF THE INVENTION

It is therefore an objective of the invention to provide a disposable diaper having padded waist and leg areas. The padding as herein disclosed covers the the plastic waistline band from inside to outside of the diaper when worn by the baby. The padding may be in the form of strips of soft pliable material, such as cotton and the like, and extends substantially around the waist. The soft padding protects the infant and toddler from scratches, irritations, and abrasions commonly inflicted by known diaper designs. The strip of padding further performs the added function of inhibiting leakage from within the diaper. The protection provided by the padding not only exists within the waist line portion of the diaper, but is also present at the top and outside of the diaper where the skin may overlap when worn.

The disposable diaper herein disclosed further includes strips of soft material, such as cotton and the like, at the edge portions of the diaper that surround the legs of the wearer to accomplish similar functions as the padding at the waist areas.

DESCRIPTION OF THE PREFERRED EMBODIMENT

Figure 1:
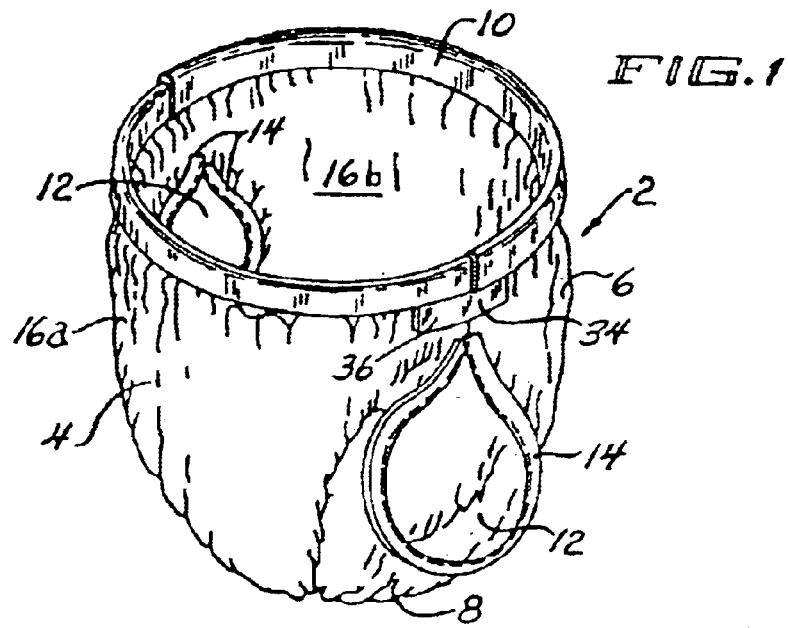
FIG. 1 is a perspective view, with parts of the wasitline padding removed, of the disposable diaper of the invention.

Referring now to FIGS. 1–4, this is illustrated the disposable diaper with padded waistline and legholes of the invention, generally designated by reference numeral 2. In its closed configuration as it is worn in the form of FIG. 1, the diaper 2 is formed with a typical front section 4, a back section 6, a crotch area 8, and a top portion 10 forming an adjustable waistline construction. Leg holes 12 are defined by edge portions 14 of disposable diaper 2. The diaper 2 is formed in multiple superimposed sheets of material in front section 4, back section 6 and crotch area 8, including an outer liquid impervious outer sheet 16a and an inner liquid permeable sheet 16b as is well known. One or more layers 18 (FIGS. 3 and 4) of a liquid absorbent material, such as cotton, pulp and the like, is imposed between the outer sheet 16a and the inner sheet 15b as is conventional. The thickness of inner material 18 may be thickened in the crotch area 8 and elsewhere for greater liquid absorption.

Figure 2:
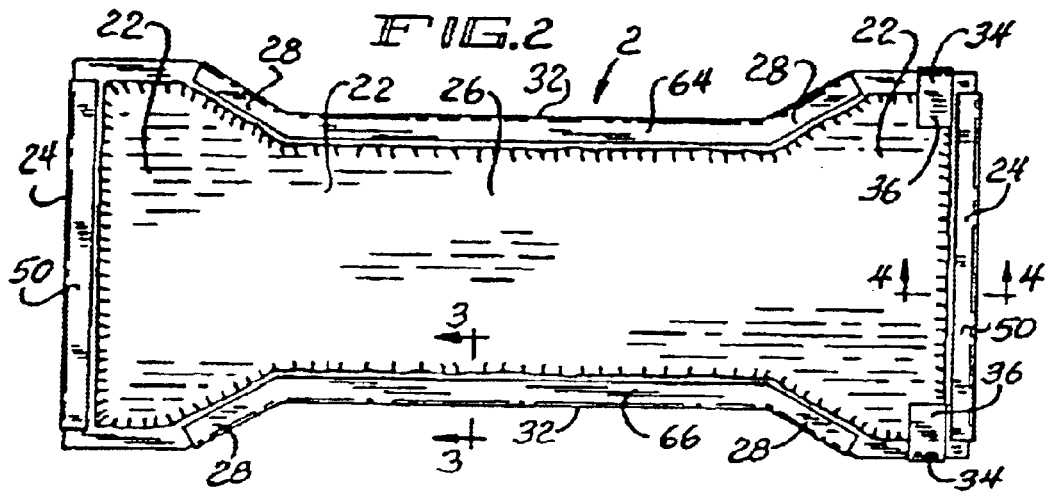
FIG. 2 is a rear plan view showing the inside of the diaper of FIG. 1 in a flat configuration.

The diaper 2 in its flat configuration as shown in FIG. 2 is formed as a single body 20 having enlarged end portions 22 which terminate at edges 24 that form the top waist band portion 10 shown in FIG. 1. The intermediate section 26 of body 20 includes tapered edges 28 and a central section. having opposed edges 32 that form the edge potions 14 of the leg holes 12. A pair of plastic adhesive strips 34 and the like having a detachable free end 36 are affixed on one enlarged end portion 22 of the body 20 to permit the diaper 2 to be adjustably affixed to the opposite end portion 22 to secure the diaper to the infant as in the configuration shown in FIG. 1.

Figures 3, 4:
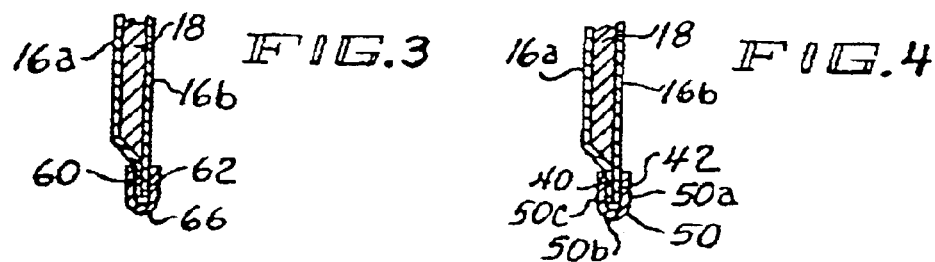
FIG. 3 is a partial end view, with parts in section, showing the portion of the diaper forming the legholes in the configuration of FIG. 1.
FIG. 4 is an end view, with parts in section, showing the edge portions of the diaper forming the waist band areas.

Referring now to FIGS. 1,2, and 4, the waistline portion 10 is formed by border sections 40,42 of the inner and outer sheets 16a and 16b which are affixed together. The border sections 40, 42 are fabricated from a plastic material or similar material. A outer strip 50 of soft material in the form of a strip of cotton or other non-abrasive material is bent lengthwise over the border sections 40,42 of a plastic material and the like located on each of the enlarged sections 22 in FIG. 2 in affixed relationship by an suitable technique of attachment. The strip 50 forms surfaces 50a, 50b, and 50c that are respectively positioned from inside to outside of the diaper 2 so as to provide a soft cushion or pad substantially over the exposed surfaces of border sections 40,42 to protect the skin of the infant or toddler and provide an additional absorbent barrier to alleviate leakage. The strip 50 may be formed as a pair of strips to generally extend 360 degrees at the waist in the configuration of FIG. 1 (one of the strips 50 being cut away in FIG. 1 for illustrative purposes).

Referring again to FIGS. 1,2 and 4, the edge portions 12 for leg holes 14 are similarly constructed as the waist band as previously described. The plastic borders 60,62 are affixed together (FIG. 3) and are covered in affixed relationship by strips 64, 66 of a soft material, such as cotton, to cover the exposed surfaces of borders 60,62 to serve the same function at leg holes 14 as soft strips 60 at the waist band.

What is claimed is:

1. A disposable diaper comprising
   a body portion having two enlarged end portions and a narrowed intermediate portion therebetween, the body portion being shaped so that said diaper may extend about a waist and crotch of a wearer and have an inside and an outside with respect to the wearer;
   each end portion having respective waistband portion at an edge thereof so that when the diaper is worn, the waistband portions gird the waist of the wearer;

at least two body-portion layers including a layer of liquid-absorbent material and a plastic layer having an edge at the edge of the diaper;

a soft padding member located along at least one of said waistband portions, being adjacent to said plastic layer edge, the soft padding member being distinct from all of said body-portion layer, the soft padding member including a material formed from a soft substance so that the soft substance is located between the diaper wearer and the plastic layer edge, so that the diaper presents a soft surface at said inside of the diaper waistband portion despite said plastic layer edge; and said soft padding member extending from the inside to the outside of said diaper, wrapping over said plastic layer edge, providing cushioning and a barrier to alleviate leakage.

2. A disposable diaper comprising a body portion having two enlarged end portions and a narrowed intermediate portion therebetween, the body portion being shaped so that said diameter may extend about a waist and crotch of a wearer and have an inside and an outside with respect to the wearer;

each end portion having respective waistband portion at an edge thereof so that when the diaper is worn, the waistband portions grid the waist of the wearer;

at least two body-portion layers including a layer of liquid-absorbent material and a plastic layer having an edge at the edge of the diaper;

a strip of non-abrasive material located along at least one of said waistband portions, being substantially adjacent to said plastic layer edge, said strip being distinct from all of said body-portion layer, said strip providing a cushion between the diameter wearer and the plastic layer edge so that the diaper presents a cushioned surface at said inside of the diaper waistband portion despite said plastic layer edge; and said strip extending from the side of the diaper to the outside of the diaper, wrapping over said plastic layer edge, providing cushioning and a barrier to alleviate leakage.

* * * * *